United States Patent [19]

Gould et al.

[11] Patent Number: 4,552,554

[45] Date of Patent: Nov. 12, 1985

[54] INTRODUCING CATHETER

[75] Inventors: Arnold S. Gould, Bedford, Mass.; Gary Sawicki, Thompson, Conn.; Michael A. Ciannella, Marlboro, Mass.

[73] Assignee: Medi-Tech Incorporated, Watertown, Mass.

[21] Appl. No.: 624,053

[22] Filed: Jun. 25, 1984

[51] Int. Cl.$^4$ .................. A61B 17/00; A61M 5/00
[52] U.S. Cl. .................. 604/51; 604/104; 604/164; 604/264; 604/280
[58] Field of Search .......... 604/104, 164, 170, 280, 604/51-53; 128/778, 657, 658

[56] References Cited

U.S. PATENT DOCUMENTS

| | | | |
|---|---|---|---|
| 1,968,997 | 8/1934 | Drucker | 174/177 |
| 2,118,631 | 5/1938 | Wappler . | |
| 2,164,926 | 7/1939 | Kleine | 604/170 |
| 2,856,934 | 10/1958 | Petillo . | |
| 2,922,420 | 1/1960 | Cheng . | |
| 3,539,034 | 11/1970 | Tafeen . | |
| 3,749,136 | 7/1973 | Slingluff et al. . | |
| 3,804,097 | 4/1974 | Rudie . | |
| 4,230,123 | 10/1980 | Hawkins, Jr. . | |
| 4,305,314 | 9/1983 | Cope | 604/51 |
| 4,306,562 | 12/1981 | Osborne . | |

FOREIGN PATENT DOCUMENTS 2605590 8/1977 Fed. Rep. of Germany .

Primary Examiner—Stephen C. Pellegrino

[57] ABSTRACT

An introducing catheter for use in placing a large guidewire after a small guidewire is in position. The catheter has a tapered distal tip, decreased lumen size at the distal end, a side port and a ramp disposed within the tube at the distal end of the side port. The ramp is inclined distally toward the side port, the distal end of the ramp being fixed to the tube adjacent to the side port and the proximal end of the ramp being disposed adjacent the inner wall of the tube in the region opposite the side port in the manner that the small guidewire can move proximally past the ramp. The ramp deflects the distally moving larger wire so that it exists through the side port. In the embodiment shown, the ramp is formed integrally of low friction thermoplastic (PTFE) and the upper surface of the proximal end of the ramp has a convex, wire-deflecting contour as a result of thermoforming pressure.

16 Claims, 14 Drawing Figures

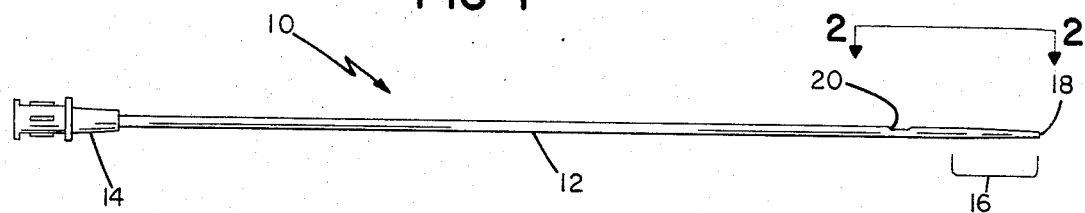
FIG 1
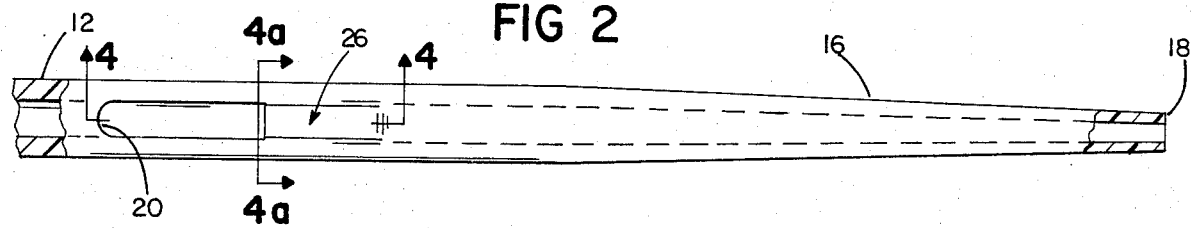
FIG 2
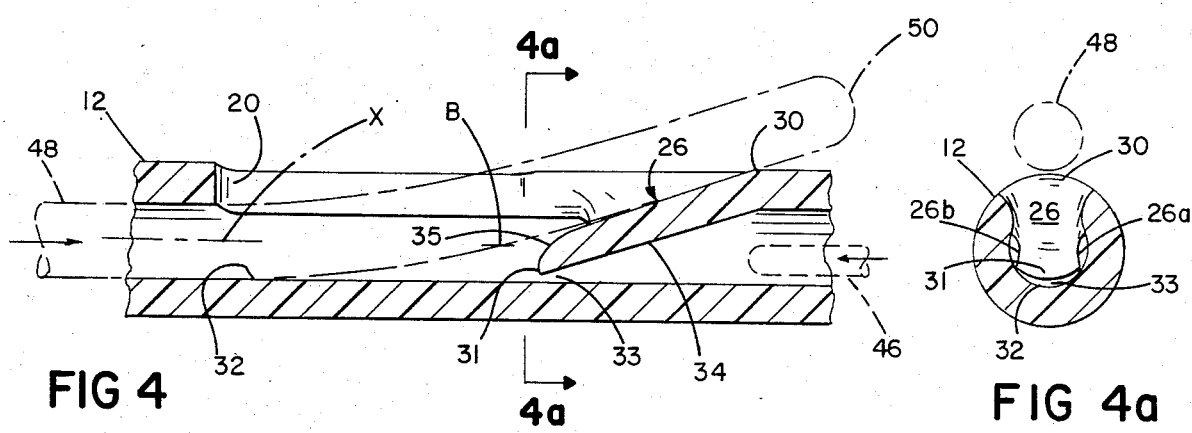
FIG 4
FIG 4a
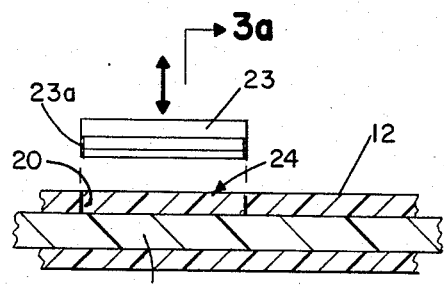
FIG 3
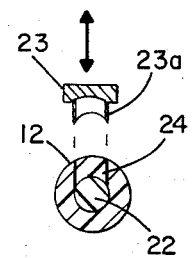
FIG 3a
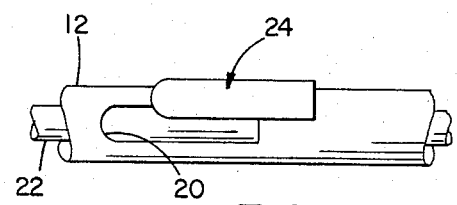
FIG 3b
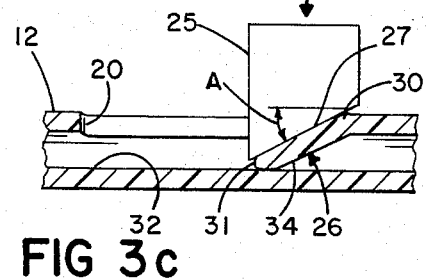
FIG 3c
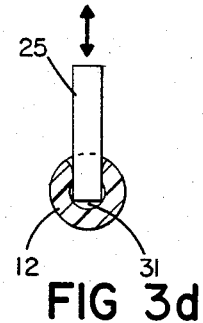
FIG 3d
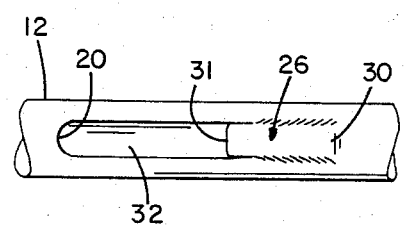
FIG 3e

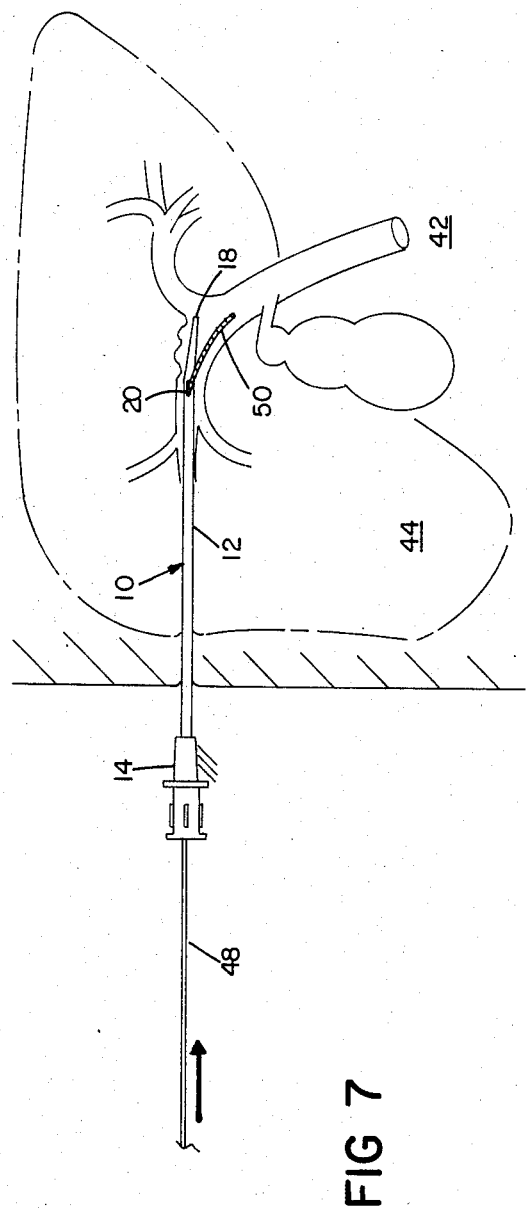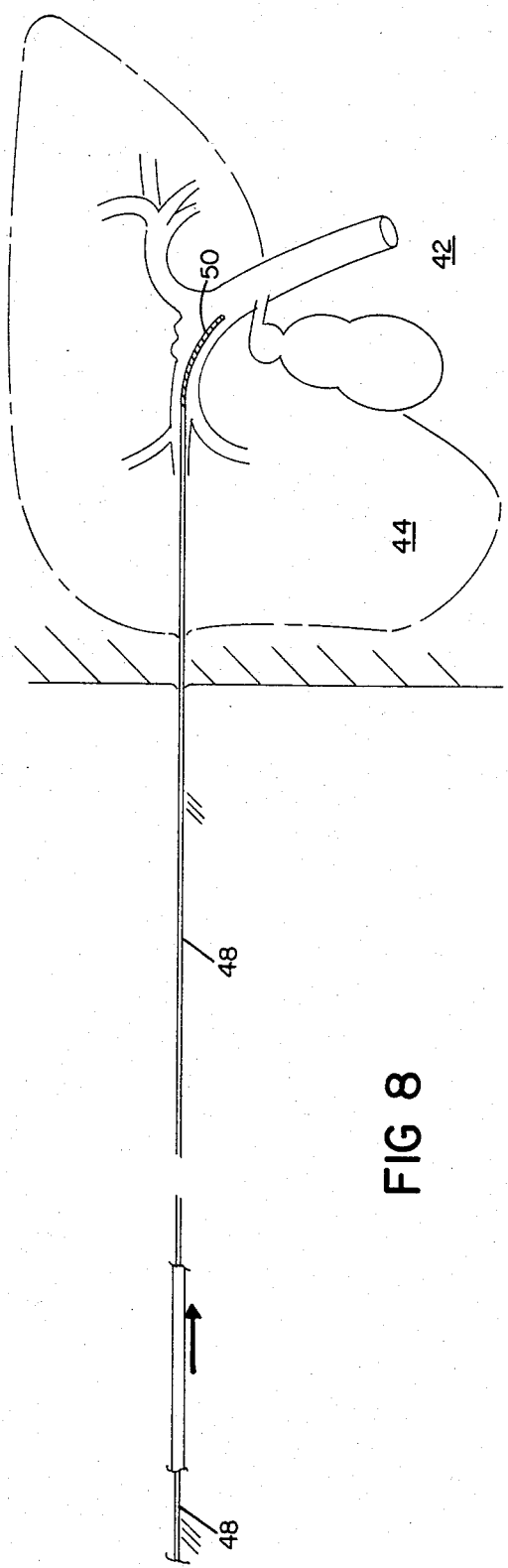

INTRODUCING CATHETER

The invention relates to devices known as introducing catheters which are used as intermediate aids in catheterization of the body.

In one procedure for introducing large bore drainage catheters into organs such as the liver, the kidneys or biliary ducts, a hollow needle is inserted through flesh of the body to position the tip within the desired organ. A guidewire is advanced through the needle bore until its tip enters the organ and then the needle is withdrawn. Fascial dilators are then advanced over the guidewire to enlarge the opening in the flesh sufficiently for introduction of the large bore drainage catheter.

To minimize trauma it has been known to employ in succession a fine needle and guidewire, a tapered introducing catheter, a larger guidewire and then the desired catheter. By this means only a small needle puncture is required for the initial exploration, hence damage and trauma can be minimized if more than one attempt is required before the needle tip is correctly positioned. Special orientation and bending of the devices have been required for placing the larger guidewire in such procedures. In one example, Cope U.S. Pat. No. 4,405,314, the introducing catheter is curved and has a side port distal to the curve, located on the inside of the curve. The larger of the guidewires must be a j-wire. Introduced from the proximal end, this wire is caused by the curve in the catheter to orient itself in a manner that causes the distal tip of the j-wire to exit from the side port.

It is an object of the present invention to provide an improved and versatile introducing catheter that permits use with both floppy tip and straight guidewires, as well as j-type guidewires, and does not require either special bending of tubes or special orientation in order to correctly place the tip of the large guidewire.

SUMMARY OF THE INVENTION

The introducing catheter of the invention comprises a tube defining a lumen and having proximal and distal open ends, the tube having a tapered tip and decreased lumen size at the distal end, the catheter enabling distal entry of a first relatively small diameter guidewire, the tube further having a side port larger than the distal diameter of the lumen through which a larger, second guidewire, advanced with the tube from the proximal end, can emerge. According to the invention, a ramp is disposed within the tube at the distal end of the side port, the ramp being inclined distally toward the side port, the distal end of the ramp being fixed to the tubing adjacent to the side port and the proximal end of the ramp being disposed adjacent to the inner wall of the tubing in the region opposite the side port in a manner to permit passage therepast of the first, relatively small diameter guidewire, the ramp thereby being adapted to permit the first guidewire to be advanced proximally through the tubing from the distal tip, and the ramp being adapted to deflect the tip of the second, larger diameter guidewire advanced distally through the tubing from the proximal end, to cause the second guidewire to emerge from the lumen via the side port.

In preferred embodiments, the second guidewire is a straight, floppy-tip, or j-type guidewire; the ramp is formed integrally with the tube, preferably the ramp being a deformed portion of the wall of the tube; and the proximal end of the ramp is disposed at a predetermined limited distance from the inner wall of the tubing in the region opposite the side port to enable passage of the first guidewire.

According to another aspect of the invention, a kit used for introducing a large bore drainage catheter into an organ of the body comprises: a hollow thin wall needle, the needle having a lumen therethrough, a stylet for the needle, sized and adapted to extend through the needle lumen, a first, relatively small guidewire having a diameter sized to permit it to be received with the lumen of the needle; an introducing catheter as described above; a stiffening cannula defining a lumen and having proximal and distal open ends, the cannula being sized to be received within the introducing catheter and having an outer diameter which is larger than the lumen of the introducing catheter at the distal end, the lumen of the cannula being sized to receive the first guidewire therethrough; and a second, larger guidewire having a diameter substantially larger than the diameter of the first guidewire and of the lumen of the introducing catheter at the distal end, the second guidewire being sized to pass through the proximal end and the side port of the introducing catheter.

In preferred embodiments of this aspect of the invention, the needle is a 21 gauge needle, the first guidewire has a diameter of the order of about 0.018 inch, and the second guidewire has a diameter of the order of about 0.038 inch.

According to still another aspect of the invention, a method for inserting a catheter into a body cavity comprises the steps of: (1) percutaneously inserting a needle having a lumen into a desired position projecting into the body cavity; (2) inserting a first, relatively small diameter guidewire through the lumen of the needle so that it projects from the distal end of the needle into the body cavity; (3) withdrawing the needle from the first guidewire while maintaining the guidewire within the body cavity; (4) advancing the introducing catheter as described above over the first guidewire to the desired position within the body cavity while maintaining the position of the first guidewire relative to the body cavity, the guidewire passing beneath the ramp of the catheter; (5) removing the first guidewire from the introducing catheter while maintaining the introducing catheter in its position relative to the body cavity; (6) inserting into the introducing catheter a second guidewire having a diameter significantly greater than the lumen of the introducing catheter at the distal end; (7) causing the second guidewire to emerge through a side port in the introducing catheter by causing the guidewire to engage upon the inclined surface of the ramp at the distal end of the side port to be deflected from the side port; (8) removing the introducing catheter from the second guidewire while maintaining the position of the guidewire relative to the body; and (9) advancing a drainage catheter over the second guidewire to a desired position with the body cavity while maintaining the position of the guidewire relative to the body.

In preferred embodiments, the method includes inserting a stiffening cannula into the introducing catheter prior to advancing this catheter over the first guidewire, step 4 includes advancing the stiffening cannula with the introducing catheter received thereover, over the first guidewire to a desired position with the distal end of the cannula in the body cavity while maintaining the position of the first guidewire relative to the body cavity; and step 5 includes removing the cannula and the first guidewire from the introducing catheter while maintaining the introducing catheter in its position relative to the body cavity.

According to still another aspect of the invention, an introducing catheter combination comprises the introducing catheter tube described above and a stiffening cannula received within the tube and terminating proximally of the ramp, the cannula being removable from the tube. In preferred embodiments, the combination further comprises a guidewire received within the catheter tube and stiffening cannula and having a diameter approximately the same as the lumen at the distal end of the catheter.

According to another aspect of the invention, the introducing catheter described above is formed at the distal end of the side port out of material of the tube, the distal end of the ramp being integral with the tube and the proximal end of the ramp being free, the forming proceduring including depressing a portion of the tube distal of the port inward to a position adjacent the inner wall of the tube and setting this portion at an incline, whereby the ramp permits the first guidewire to be advanced proximally through the tube from the distal tip under the ramp, past the side port and out of the proximal end and the ramp can deflect the tip of the second, larger diameter guidewire advanced distally through the tube from the proximal end to cause the second guidewire to emerge from the lumen via the side port.

In one preferred embodiment, the forming step comprises pressing a heated forming tool against the tube adjacent to the side port, preferably the heated tool serving to press the tip of the ramp against the bottom of the bore so that heat and concentrated pressure deform the upper edge of the proximal end of the ramp into a convex, wire-deflecting curvature.

PREFERRED EMBODIMENT

We first briefly describe the drawings.

DRAWINGS

FIG. 1 is a side view of the introducing catheter of the invention;

FIG. 2 is an enlarged plan view of the side port at the line 2—2 of FIG. 1;

FIGS. 3, 3a and 3b are somewhat diagrammatic longitudinal section, transverse section and perspective views showing formation of the side port, while FIGS. 3c, 3d and 3e are similar views, respectively, showing formation of the ramp;

Figure 5:
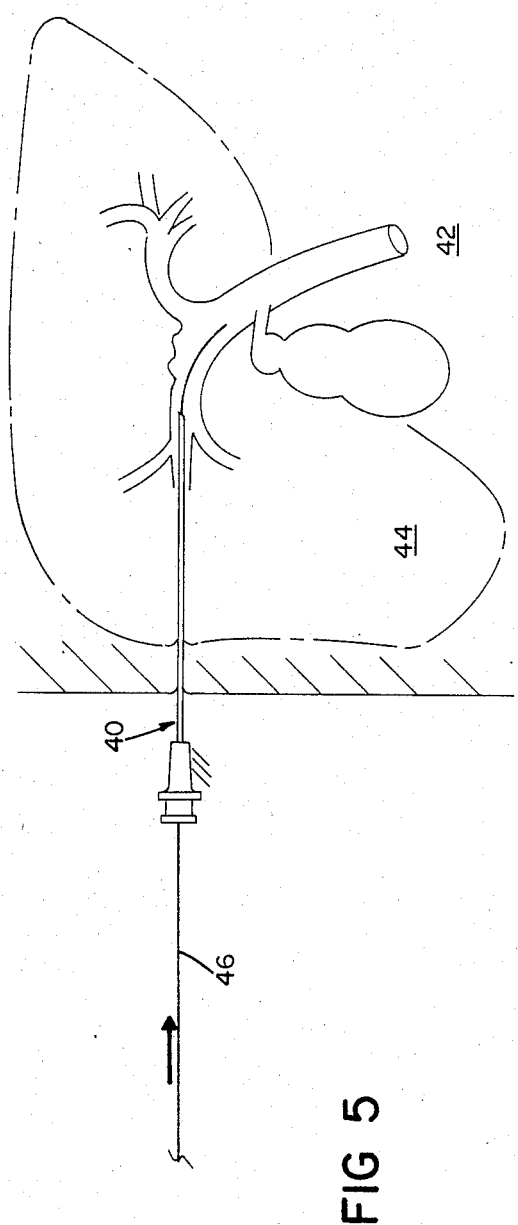

FIG. 4 is an enlarged longitudinal section view of the port at the line 4—4 of FIG. 2, while FIG. 4a is a transverse section view at the line 4a—4a of FIG. 4; and FIGS. 5, 6, 7 and 8 are sequential diagrammatic views showing one procedure employing the introducing catheter of the invention.

Referring to FIG. 1, the main length of introducing catheter 10 comprises tube 12, typically 6 French (0.079 inch outer diameter) tubing of FEP polymer (Dupont's Teflon), a thermoplastic about 9 inches long with 0.020 inch wall thickness. Luer taper fitting 14 is injection molded onto the proximal end of tube 12 to facilitate manipulation and positioning of the catheter. The distal portion of tube 12 is drawn into a tapering tip 16, e.g., about 0.8 inch long, with the inner diameter decreasing from about 0.040 inch to 0.020 inch over that length, and the wall thickness decreasing to about 0.008 inch at the extreme tip 18.

Proximally positioned from the tapering portion, e.g. about 1.1 inches from the distal tip, side port 20 (FIG. 2) is defined through the side wall of tube 12.

Referring to FIG. 3 et seq., the steps of the forming operations for the side port and ramp forming operations are shown. In FIGS. 3 and 3a, nylon mandrel 22 having diameter approximately equal to the inner diameter of tube 12 is inserted into the tube to extend beneath the position where side port 20 is to be formed. Die 23 having blade 23a extending continuously about its periphery is pressed downward against the mandrel surface to sever segment 24, e.g. of length of about 0.16 inch and width of about 0.040 inch, approximately equal to the inner diameter of the tube, from the surrounding tube surface. The die is retracted and segment 24 (FIG. 3b) is removed.

In a second operation (FIGS. 3c and 3d), a heated forming tool 25 having an inclined surface 27 is pressed against the wall of the tube, the tool extending distally from the distal end of the side port about 0.125 inches. As the heated tool 25 presses downward, the portion 26 of heated tube material 30 beneath the tool is depressed to angle A corresponding to that of tool surface 27, i.e. about 25 degrees. The forming apparatus may be set to press the proximal end 31 of portion 26 into contact with the bore opposed surface, to concentrate maximum forming pressure on the proximal upper edge. The tool dwells sufficiently to heat-set the plastic, to give the upper edge the convex wire-deflecting contour shown in FIG. 4. When the tool retracts the ramp returns slightly upwardly to the angle of FIG. 4, adhesion being prevented at the tip by selection of non-stick materials under the conditions of formation (preferably PTFE). Thus a gap 33 of predetermined limited size is left between the end of portion 26 and the inner surface 31 of the tube opposite the side port, adapted to enable passage of the small guidewire but not the large guidewire. Preferably the upper portion B of the end of the ramp does not lie above axis X of the catheter. The result is a proximally-directed, distally inclined ramp fixed at the distal end of the side port that obstructs most but not all of the cross-section of the tubular passage. The curvature of the inner surface of the tubing and the width of portion 26 relative to the tube diameter can affect the size of the gap 33. By selection of the various parameter a desired gap 33, selected between e.g. about 0.005 to 0.020 inch in height can be obtained. The material of the ramp is resilient and capable of locally deflecting slightly upwardly under force of sufficient magnitude applied to the under-surface 34 of the ramp as by a wire inserted from the distal end. Thus a distally inserted guidewire of slightly larger size than gap 33 can gain passage through the cannula. On the other hand, the stiffness of the ramp material and the support provided to its longitudinal edges by the integral tube walls enables the ramp to offer resistance to a force directed longitudinally against the proximally-directed surface 35 of the ramp, e.g. by a proximally introduced guidewire that is thrust distally against the ramp. Under such conditions the angle of the ramp is effective to cause the end of the wire to be deflected out of port 20.

By way of example, a typical procedure using the introducing catheter of the invention, in this case introduction into a person's liver, will now be described.

Referring to FIG. 5, a 21 gauge (0.46 mm diameter) needle 40 containing a stylet (not shown) extending through the length of the needle bore is inserted precutaneously into the body 42 of the patient and into the liver 44. The stylet is removed and an opaque dye is injected through the needle to allow the position of its tip to be determined. If the tip is not correctly positioned, the needle is withdrawn and the steps repeated.

When correctly positioned, a small gauge guidewire 46, e.g., 0.018 inch diameter, is inserted through the needle until its distal end projects into the liver. The needle is then withdrawn over the guidewire while the wire remains in place.

Figure 6:
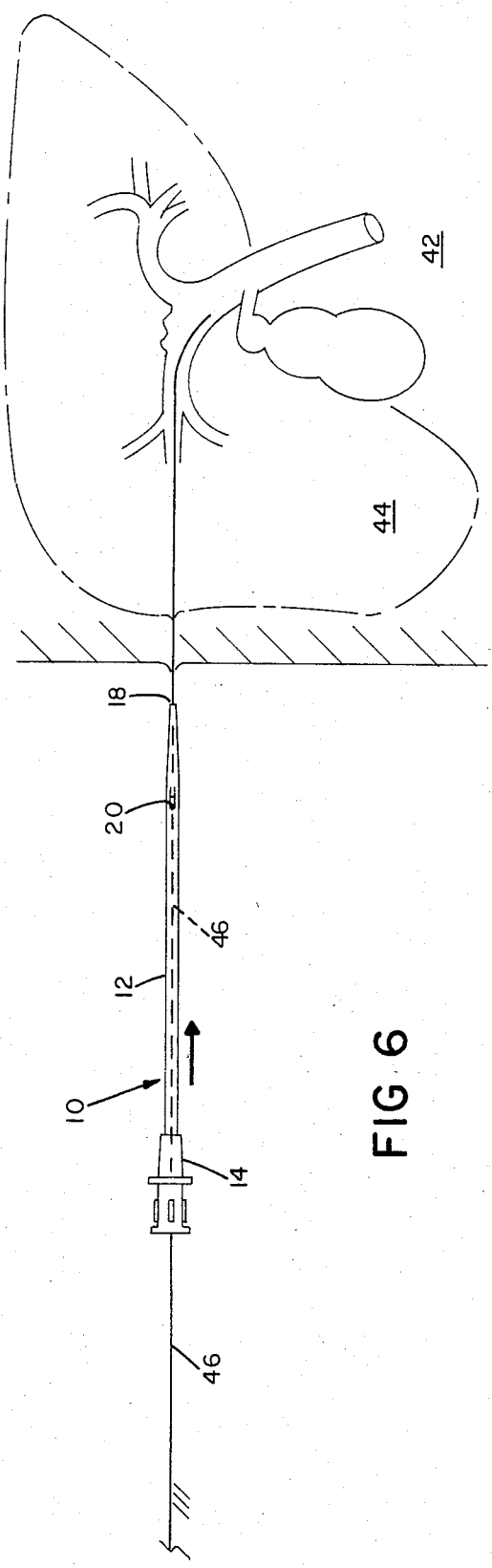

Referring to FIG. 6, the distal tip 18 of introducing catheter 10 of the invention is placed over the proximal end of the guidewire 46 and the catheter is advanced distally along the wire. A stiffening cannula (not shown) about 20 gauge (0.035 inch diameter) is inserted into the proximal portion of the catheter. When the proximal end of the guidewire relatively approaches and engages upon the undersurface (34, FIG. 4) of ramp 26, the end of the wire is deflected downward toward the lower surface 32 of the tube to pass through gap 33 below the proximal end 31 of the ramp. The ramp being formed of resilient material can deflect locally upward slightly to allow passage in the proximal direction of the small guidewire 46.

The introducing catheter is advanced along guidewire 46 until the side port 20 is within the liver 44 (FIG. 7). The guidewire 46 and the stiffening cannula are then withdrawn.

A second, larger diameter guidewire 48, e.g. 0.038 inch diameter, shown to be of the straight, floppy-tip type, is inserted into the introducing catheter 10 and advanced in the distal direction. The floppy tip 50 is advanced until it engages upon the distally-directed, inclined surface 35 of ramp 26. The ramp deflects the tip 50 upward and out of port 20. It is noted that the gap beneath the ramp is too small to permit passage of the guidewire tip 50 distally beyond the ramp. Should the tip of the guide wire engage upon the proximal end 31 of ramp 26, this engagement resists axial movement of the guidewire and causes the guidewire to bow outward and exit side port 20. The low-friction nature of the fluorocarbon plastic of which the tube is made helps in this action.

The introducing catheter 10 is then withdrawn along the guidewire 48 (FIG. 8). This large guidewire is then employed for introduction of large bore drainage catheters (not shown) by standard procedures.

The embodiment just described functions well when the floppy-tip guidewire 46 is replaced with a straight wire or with a j-wire of sufficient radius relative to the tube inner diameter. In the latter case, the ramp generally functions to enable exit of the j-tip through the port regardless of orientation of the "j" formation.

Other embodiments of the invention are within the following claims.

What is claimed is:

1. In an introducing catheter comprising: a tube defining a lumen and having proximal and distal open ends, said tube having a tapered tip and decreased lumen size at said distal end, said catheter enabling distal entry of a first relatively small diameter guidewire, said tube further having a side port larger than the distal diameter of said lumen through which a larger, second guidewire, advanced within said tube from said proximal end, can emerge.

the improvement wherein a ramp is disposed within said tube at the distal end of said side port, said ramp being inclined distally toward said side port.

the distal end of said ramp being fixed to said tubing adjacent to said side port and the proximal end of said ramp being disposed adjacent to the inner wall of said tubing in the region opposite said side port in a manner to permit passage therepast of said first, relatively small guidewire.

said ramp thereby being adapted to permit said first guidewire to be advanced proximally through said tubing from the distal tip past said side port and said ramp being adapted to deflect the tip of said second, larger diameter guidewire advanced distally through said tubing from the proximal end, to cause said second guidewire to emerge from said lumen via said side port.

2. The introducing catheter of claim 1 wherein said second guidewire is a straight, floppy-tip or j-type guidewire.

3. The introducing catheter of claim 1 wherein said ramp is formed integrally with said tube.

4. The introducing catheter of claim 3 wherein said ramp comprises a deformed portion of the wall of said tube.

5. The introducing catheter of claim 1 or 4 wherein a gap of predetermined limited dimension is defined between the end of said ramp and the inner wall of said tube for passage of said first guidewire.

6. A kit used for introducing a drainage catheter into an organ of the body comprising:
a hollow thin wall needle, said needle having a lumen therethrough,
a stylet for said needle sized and adapted to extend through said needle lumen,
a first, relatively small guidewire having a diameter sized to permit said first guidewire to be received within the lumen of said needle;
an introducing catheter including a tube defining a lumen and having proximal and distal open ends, said tube having a tapered tip and decreased lumen size at said distal end, said tube further having a side port larger than the distal diameter of said lumen and a ramp disposed within said tube at the distal end of said side port, said ramp being inclined distally toward said side port, the distal end of said ramp being fixed to said tubing adjacent to the side port and the proximal end of said ramp being disposed adjacent to the inner wall of said tubing in the region opposite said side port in a manner to permit passage therepast of said first relatively small guidewire, said lumen having a diameter at said distal end which is sufficiently large to receive therethrough said first guidewire;
a stiffening cannula defining a lumen and having proximal and distal open ends, said cannula being sized to be received within said introducing catheter and having an outer diameter which is larger than the lumen of said introducing catheter at the distal end, the lumen of said cannula being sized to receive said first guidewire therethrough; and
a second, larger guidewire having a diameter substantially larger than the diameter of said first guidewire and of the lumen of said introducing catheter at the distal end, said second guidewire being sized to be received through the proximal end and the side port of said introducing catheter.

7. The kit of claim 6, wherein said needle is a 21 gauge needle, said first guidewire has a diameter of the order of about 0.018 inch, and said second guidewire has a diameter of the order of about 0.038 inch.

8. A method for inserting a catheter into a body cavity comprising the steps of:
(1) percutaneously inserting a needle having a lumen into a desired position projecting into the body cavity;
(2) inserting a first, relatively small diameter guidewire through the lumen of the needle so that it projects from the distal end of the needle into the body cavity;
(3) withdrawing the needle from the first guidewire while maintaining the guidewire within the body cavity;
(4) advancing an introducing catheter having an internal ramp over the first guidewire to the desired position within the body cavity while maintaining the position of the first guidewire relative to the body cavity, the wire passing relatively under the ramp;
(5) removing the first guidewire from the introducing catheter while maintaining the introducing catheter in its position relative to the body cavity;
(6) inserting into said introducing catheter a second guidewire having a diameter significantly greater than the lumen of said introducing catheter at the distal end;
(7) causing said second guidewire to emerge through a side port in said introducing catheter by causing said guidewire to engage upon the inclined surface of the ramp at the distal end of said side port to be deflected from said side port;
(8) removing said introducing catheter from said second guidewire while maintaining the position of said guidewire relative to said body; and
(9) advancing a drainage catheter over said second guidewire to a desired position with the body cavity while maintaining the position of said guidewire relative to said body.

9. The method of claim 8 including
inserting a stiffening cannula into the introducing catheter prior to advancing it over the first guidewire and wherein step 4 includes
advancing the cannula with the introducing catheter received thereover, over the first guidewire to a desired position with the distal end of the cannula in said body cavity while maintaining the position of the first guidewire relative to the body cavity;
and step 5 includes removing the cannula and the first guidewire from the introducing catheter while maintaining the introducing catheter in its position relative to the body cavity.

10. An introducing catheter combination comprising:
(a) a tube formed of resilient material defining a lumen and having proximal and distal open ends, said tube having a tapered tip and decreased lumen size at said distal end, said tube further having a side port and a ramp disposed within said tube at the distal end of said side port, said ramp being inclined distally toward said side port, the distal end of said ramp being fixed to said tube adjacent to said side port and the proximal end of said ramp being disposed adjacent to the inner wall of said tube in the region opposite said side port in a manner to permit passage therepast of said first relatively small guidewire, said lumen having a diameter at said distal end which is substantially smaller than said side port; and
(b) a stiffening cannula received within said tube and terminating proximally of said ramp, said cannula being removable from said tube.

11. The introducing catheter combination of claim 10 and further comprising:
(c) a guidewire received within said tube and cannula and having a diameter approximately the same as the lumen at the distal end of said catheter.

12. A method of forming an introducing catheter comprising
providing a tube defining a lumen having proximal and distal open ends,
forming a side port in said tube larger than the distal diameter of said lumen, and
forming a ramp within said tube at the distal end of said side port, out of material of said tube,
the distal end of said ramp being integral with said tube and the proximal end of said ramp being spaced from the opposed portion of the inner wall of said tube, said ramp-forming step including
depressing the proximal end of said ramp inward to a position spaced from the inner wall of said tube in the region opposite said side port, and
setting said ramp at said incline,
whereby said ramp permits said first guidewire to be advanced proximally through said tube from the distal tip past said ramp and side port and out of said proximal end and said ramp can deflect the tip of said second, larger diameter guidewire advanced distally through said tube from the proximal end to cause said second guidewire to emerge from said lumen via said side port.

13. The method of claim 12 wherein said tube comprises thermoplastic and wherein said forming and depressing are performed by pressing a heated forming tool having an inclined surface against a portion of said tube adjacent to said side port, said heating causing the deformed portion to be set at said incline.

14. In an introducing catheter comprising: a tube of low-friction thermoplastic defining a lumen and having proximal and distal open ends, said tube having a tapered tip and decreased lumen size at said distal end, said catheter enabling distal entry of a first relatively small diameter guidewire, said tube further having a side port larger than the distal diameter of said lumen through which a larger, second guidewire, advanced within said tube from said proximal end, can emerge.
the improvement wherein
a thermoformed ramp is disposed within said tube at the distal end of said side port, said ramp being inclined distally toward said side port,
the distal end of said ramp being integral with said tubing adjacent to said side port and the proximal end of said ramp being resilient and disposed adjacent to the inner wall of said tubing in the region opposite said side port in a manner to permit passage therepast of said first, relatively small guidewire.
the upper edge of the proximal end of said ramp lying at or below the center line of said tube,
said ramp thereby being adapted to permit said first guidewire to be advanced proximally through said tubing from the distal tip past said side port and said ramp being adapted to deflect the tip of said second, larger diameter guidewire advanced distally through said tubing from the proximal end, to cause said second guidewire to emerge from said lumen via said side port.

15. The catheter of claim 14 wherein said tube comprises PTFE.
16. The catheter of claim 14 or 15 wherein the upper surface of the proximal end of said ramp is convexly curved as a result of thermoforming pressure.

* * * * *